United States Patent
Kalinin et al.

(10) Patent No.: US 7,259,139 B1
(45) Date of Patent: Aug. 21, 2007

(54) MEANS FOR MAINTENANCE AND/OR CORRECTION OF GLUCOSE CONCENTRATION IN BLOOD

(75) Inventors: Iouri Tikhosovich Kalinin, Moscow (RU); Anatoly Borisovich Davydov, Moscow (RU); Boris Ivanovich Leoniv, Moscow (RU); Tatjana Igorevna Solodkaya, Moscow (RU); Gennadiy Ljvovich Khromov, Moscow (RU); Iouri Gennadievich Bobkov, Moscow (RU)

(73) Assignee: Frohwitter, Munich (DE)

( * ) Notice: Subject to any disclaimer, the term of this patent is extended or adjusted under 35 U.S.C. 154(b) by 0 days.

(21) Appl. No.: 10/297,004

(22) PCT Filed: May 26, 2000

(86) PCT No.: PCT/EP00/04826

§ 371 (c)(1),
(2), (4) Date: Oct. 3, 2005

(87) PCT Pub. No.: WO01/91784

PCT Pub. Date: Dec. 6, 2001

(51) Int. Cl.
*A61K 38/28* (2006.01)
*A61K 9/58* (2006.01)

(52) U.S. Cl. ............ 514/4; 424/435; 424/462

(58) Field of Classification Search .......... None
See application file for complete search history.

(56) References Cited

U.S. PATENT DOCUMENTS

| | | | | |
|---|---|---|---|---|
| 4,529,589 | A * | 7/1985 | Davydov et al. | 424/468 |
| 4,666,704 | A * | 5/1987 | Shalati et al. | 424/424 |
| 4,913,908 | A * | 4/1990 | Couvreur et al. | 424/501 |
| 5,310,558 | A * | 5/1994 | Pozzi et al. | 424/476 |
| 6,201,065 | B1 * | 3/2001 | Pathak et al. | 525/90 |
| 6,277,410 | B1 * | 8/2001 | Kabanov et al. | 424/486 |

OTHER PUBLICATIONS

Peracchia et al., "Stealth PEGylated polycyanoacrylate nanoparticles for intravenous administration and splenic targeting." J. Cont. Rel., 1999, 60, 121-8.*

* cited by examiner

*Primary Examiner*—Cecilia J. Tsang
*Assistant Examiner*—Christina Marchetti Bradley
(74) *Attorney, Agent, or Firm*—Lahive & Cockfield, LLP; Maria Laccotripe Zacharakis

(57) ABSTRACT

The invention relates to preparations that are useful in maintaining mammalian blood glucose concentrations. These preparations contain insulin, and a polymeric matrix. The polymeric matrix has a core of biodegradable, hydrophobic polymer, and an outer shell of a biodegradable, hydrophobic polymer. Alternately, the formulations contain insulin, a polymeric matrix, and a histone.

18 Claims, 1 Drawing Sheet

SCHEME 1
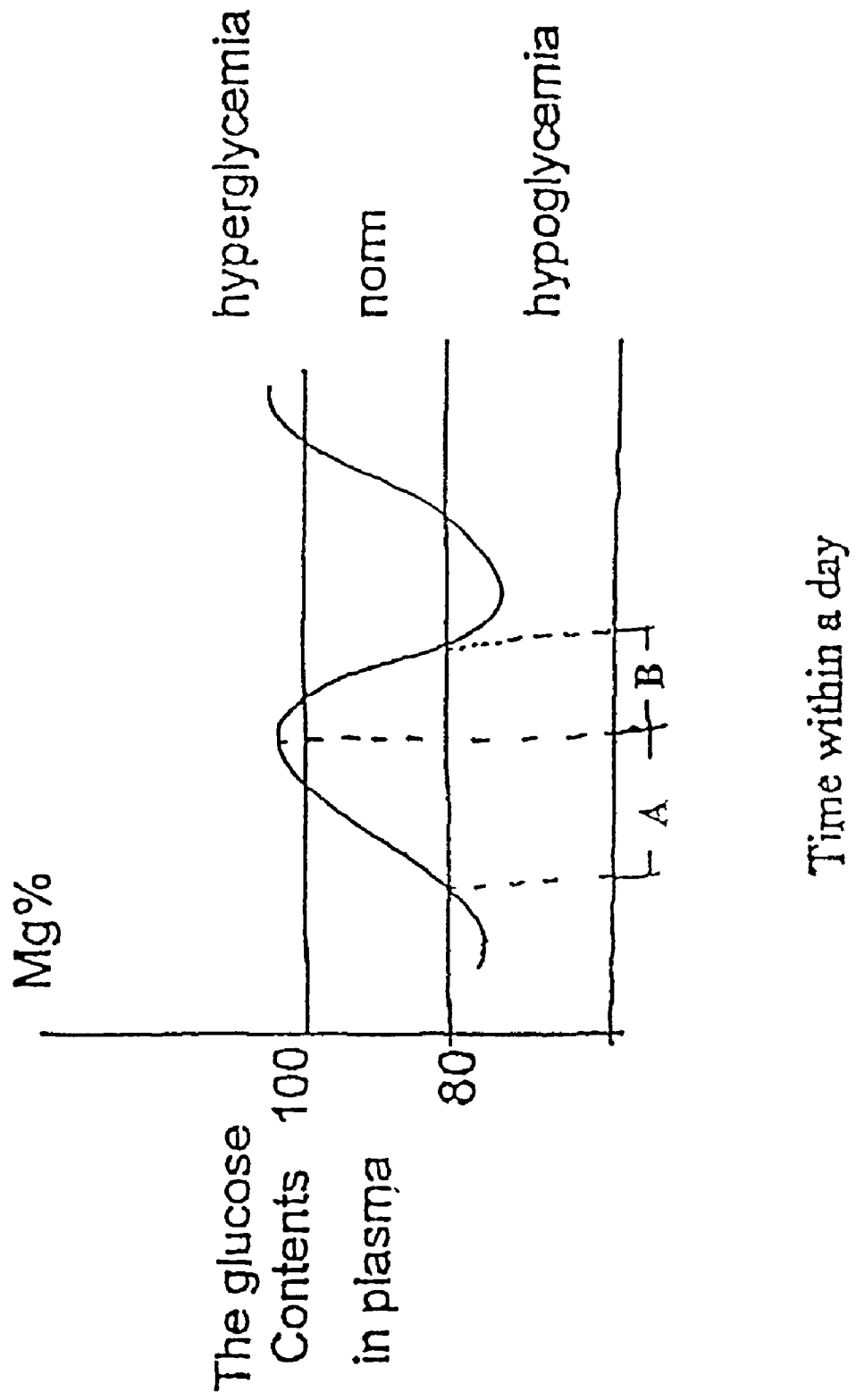

MEANS FOR MAINTENANCE AND/OR CORRECTION OF GLUCOSE CONCENTRATION IN BLOOD

GENERAL TECHNICAL BACKGROUND OF THE PRESENT INVENTION

The basic object of the present invention is to provide a technical teaching including specified means for maintenance of a constant minimum level of insulin, on the one hand, and also specified means for correction as needed of a variable component of an optimal (physiological) level of insulin in the living organism, on the other hand, and also a combination of both. In said combination, first mentioned means is to be applied for long term correction preferably, and second mentioned means is to be applied for short term correction preferably. The combined correction minimizes natural fluctuation of glucose in blood plasma of a mammal with diabetes mellitus. The changes of the glucose concentration in blood plasma are illustrated in FIG. 1.

Legend to FIG. 1:

Zone A corresponds to increase in glucose concentration in blood plasma as a result of food intake;

Zone B corresponds to decrease in glucose concentration as a result of physical activities.

During a daily cycle the glucose concentration level in blood plasma constantly changes: it raises as a result of food intake and decreases during the maintenance of the organism's vital functions subsequently. Thus, if the fluctuations go beyond certain levels determined as "norm", the complex of pathologic biochemical processes, determined as hypo- or hyperglycemia develops in the organism. As is known to the person skilled in the art, the lowest level of glucose concentration, adequate to concept "norm", meets approximately 80 mg % and top level corresponds to about 100-150 mg %. The insignificant fluctuations in certain sections of the cycle, as well as maintenance of an average normal level glucose in blood plasma in a healthy organism are regulated by the insulin produced by the pancreas. In case of a disease called diabetes mellitus the insulin level in blood is essentially reduced against norm, which effect results in a hyperglycemia of a varying level.

SUMMARY OF THE PRESENT INVENTION

In a first aspect, the present invention provides a therapeutic preparation for the maintaining a blood glucose concentration of a mammal in need thereof, the preparation comprising insulin and a polymeric matrix, said polymeric matrix comprising a core containing a biodegradable, hydrophobic polymer and an outer shell comprising a biodegradable, hydrophilic polymer.

The insulin-containing core of the preparation may have the form of a cylindrical rod or a sphere and the insulin-containing core may comprise an insoluble polymer. The insulin-containing core may comprise a biocompatible polymer selected from the group of α-cyanacrylates.

Preferably, the outer shell comprises a copolymer of N-vinylpyrrolidon and/or derivatives of acrylic- and/or methacrylic acid. The biodegradation rate of the shell is preferably lower than the biodegradation rate of the core.

A further aspect of the present invention provides a therapeutic preparation for correction of a blood glucose concentration of a mammal in need thereof, the therapeutic preparation comprising insulin, a polymeric matrix and low-molecular peptides, wherein said low-molecular peptides are histones and/or cytomedins.

Preferably, the histones and/or cytomedins have a molecular mass in the range of about 1,000-3,000 Dalton. The histones and/or cytomedins may be present in a concentration in the range 0.1-10.0 wt.-%, based on the weight of the complete therapeutic preparation. Furthermore, insulin with conditional activity of 1 mg=50 insulin units (IU) may be present according to a concentration in the range of 0.1-20.0 wt.-%, based on the weight of the complete therapeutic preparation.

The polymeric matrices used in the therapeutic preparation may comprise either copolymers of N-vinylpyrrolidone and/or acrylamide and/or ethylacrylate and/or the homopolymer of N-vinylpyrrolidon and/or polyether based on ethylene glycol and dibasic acids with a molecular mass in the range of 2,000-5,000 Dalton.

Preferably, the therapeutic preparation has the form of plates or films with a thickness in the range of 0.2-1 mm.

In a still further aspect, the present invention provides a therapeutic kit for diabetes treatment by insulin administration into a mammal's organism resulting in a continuous optimization of the glucose level in blood, the kit comprising the following components:

1.) a therapeutic preparation for maintenance of insulin concentration ensuring minimal constant therapeutic insulin level in the organism, comprising insulin and a polymeric matrix, the matrix comprising a core comprising a biodegradable, hydrophobic polymer, and an outer shell comprising a biodegradable, hydrophilic polymer; and 2.) a therapeutic preparation for correction of insulin concentration adequate to physiological fluctuations of the glucose contents in blood plasma, said therapeutic preparation comprising insulin, a polymeric matrix and histones and/or cytomedins.

A still further aspect of the invention provides a therapeutic kit for diabetes treatment by insulin administration into a mammal's organism resulting in a continuous optimization of the glucose level in blood, comprising the following components:

1.) a therapeutic preparation for long-term maintenance of insulin concentration ensuring minimal constant therapeutic insulin level in the organism, comprising insulin and a polymeric matrix, the latter comprising a core comprising a biodegradable, hydrophobic polymer, and an outer shell comprising a biodegradable, hydrophilic polymer, whereby said polymeric matrix results in biodegradation up to a proportion of not more than 50 wt.-% during a period of at least one month, preferably during a period of at least three and particularly during a period of at least seven months; and 2.) a therapeutic preparation for short-term correction of insulin concentration adequate to physiological fluctuations of the glucose contents in blood plasma, said therapeutic preparation comprising insulin, a polymeric matrix and histones and/or cytomedins.

The present invention provides a means of diabetes treatment for maintenance of a constant minimum level of insulin, on the one hand, and also specified means for correction as needed of a variable component of an optimal level of insulin in the organism, on the other hand, and also a combination of both. In said combination, first mentioned means is to be applied for long term correction preferably, and second mentioned means is to be applied for short term correction preferably.

DESCRIPTION OF PRIOR ART

Therapeutic medicaments used for treatment of diabetes are based on injecting insulin solutions which also contain stabilizing additives, preservatives, pH regulators, and components prolonging the effect of insulin. Those means are well known to the person skilled in the art and disclosed, e.g., in the prior art documents V. G. Baranov, L. Sh. Orcodeshvili; "*Guide on clinical endocrinology*", I, Medicine, 1977.

Tablets administered perorally, transdermal plasters, rectal and vaginal suppositories, and nasal sprays according to the prior art in particular have a common drawback: it is impossible to administer a precise insulin dosage due to the specific features of these medicaments, i.e., disadvantageous effect of digestive enzymes, unpredictably varying physiological properties of skin, inconveniences of usage, etc.

ORSULIN (for details, refer to "A. B. Davydov, T. I. Solodkaya, A. V. Usova, *Polymer Based Insulin Medicaments*, Collection of works of VNIIMT Institute/ВсесоюзныйНаучно-Исследовательский йИспытательныйИнститутМедипинской Техники, Труды Института, UDC 615.27:616.37:678) is used according to the state of the art fo transmucous (buccal) administration of insulin via mucous membrane of mouth cavity, transporting insulin directly into the blood current without entering the digestive system. ORSULIN is produced in plates made of biocompatible copolymers and contains insulin, preservatives and additives regulating insulin solubility and resistance to the enzymes present in the mouth cavity. Calcium glyconate and salazopyridazin (5-(para N-(3-metoxypyridazinyl-6-)-aminosulphonyl-phenylzao)salicylate) are used as the additives according to the prior art document CH-654,211-A5. Polymer matrix of ORSULIN corresponds to biocompatible hydrophilic copolymers of N-vinylpyrrolidon, acrylamide and ethylacrylate, and the homopolymer of N-vinylpyrrolidon. The matrix swells when being contacted with hydrophilic liquids and is highly adhesive to the mouth cavity surface.

All known buccal forms according to the state of the art, including ORSULIN, have a common drawback: low biological availability of insulin and the requirement to use large dosages of the drug in order to provide the desired effect. This results from the poor transport of insulin molecules through the mucous membrane of mouth cavity, thus leading to significant increased usage of the drugs.

In certain cases, mechanical devices containing insulin and releasing it into living organism, in accordance with the preliminarily fixed schedule (e.g., mini-pumps, membrane cells, etc) can be used. However, safety level of these devices is quite insufficient and possible device malfunction can result in insulin overload, giving rise to harmful and possibly fatal consequences for health and life of patients.

Polymer-based transplants also exist, containing insulin in form of solid homogenous solutions or suspensions. These transplants are used according to the state of the art in comparison with the above-discussed mechanical mini-pumps and membrane cells due to their higher safety level. In general, biologically inert, biocompatible and biosoluble polymer matrices are used for these transplants, as described in "*Drug delivery systems*"; *Chem. and Ing.*, 1985, No. 1, pp. 6-9. Insulin immobilized within these matrices permeates into the body tissues due to biodegradation or dissolution of the matrix.

Polymers biodegradable or dissoluble within body tissues are well known to the person skilled in the art as being used in therapeutic transplants, as disclosed for instance in the prior art document GB-1,462,958. This document discloses a biodegradable, implantable drug delivery device, and a process for preparing and using the same. This implantable device comprising a polymeric matrix can be especially manufactured in the form of a plate or film, a rod or fiber, a hollow cylinder, or an optionally layered rod. However, such devices cannot ensure maintenance of a certain therapy on the base of constantly releasing a drug due to the fast destruction of hydrolytically unstable polymeric matrices and a thereby resulting change of the implant surface geometry.

Polymers as silicones, etc. are well known to the person skilled in the art as being useful for medical applications, as disclosed, for instance, in the prior art document U.S. Pat. No. 3,279,996. This prior art document discloses a polysiloxane carrier for controlled release of drugs and other agents into the tissues of living human body. Therapeutic effect of these carriers according to the state of the art results from diffusion of drugs outside the inert matrix into tissue. However, carriers of this type have a significant drawback: they have to be removed surgically after their insulin supply is depleted.

Term and continuity of therapeutic effect both however depend strongly on the process of biodegradation of the polymer matrix, allowing the drug to permeate into the body tissues. Hydrophilic polymers, such as polylactides, polyglycolides, homopolymers and copolymers of $\alpha$-amino acids are proposed for use as suitable matrices of these therapeutic medicaments. These therapeutic medicaments do not have to be removed surgically after their expiration day. However, all therapeutic medicaments of this type share a common, important drawback: uniformity of drug release rate depends on the surface area of the transplant, which can change under the influence of the body environment. In order to provide the required uniformity of drug release rate during the polymer matrix degradation, various methods are proposed according to the state of the art: manufacturing cylindrical transplants with axial canal (i.e., compensating for decrease of outer surface under the influence of environment by increasing inner surface of the canal), or manufacturing multi-layered transplants with variable drug concentration levels throughout the layers. However, manufacturing these transplants according to the state of the art is highly complicated, and furthermore, swelling of the transplant due to its contact with body tissues tends to destroy uniformity of drug release rate.

A delivery system for the controlled release of macromolecules, including insulin, is described in U.S. Pat. No. 4,666,704. This system comprises a water insoluble polymer core containing a drug and a polymeric membrane coating. The polymer core may be biodegradable or non-biodegradable whilst the coating is made from water insoluble polymers containing a pore-forming agent. In use, the pore-forming agent dissolves, thereby releasing the drug from the polymer core.

DETAILED DESCRIPTION OF THE PRESENT INVENTION

1. First Aspect of the Present Invention

The first aspect of the present invention provides a means for supportive therapy of diabetes in the form of a means for the maintenance of the glucose concentration level in the blood plasma of a diabetic mammal, preferably for the long-term maintenance of said glucose concentration level.

The first problem of this invention therefore is to provide a medicine for supportive therapy of diabetes lacking the common disadvantages of the popular medicines, i.e., which does not have to be removed surgically from the body of the patient and which provides stable correction of insulin deficit, preferably long-term correction.

The above first problem is achieved by using both hydrophobic and hydrophilic, biocompatible polymers as the matrix of the medicine, which contains a suitable amount of insulin, preferably sufficient for at least 1 month or more of insulin deficit correction. The transplant consists of the insulin-containing core, preferably in form of a cylindrical rod or sphere, and the outer shell. The transplant core is manufactured of a hydrophobic, preferably insoluble polymer, particularly belonging to the polymer group of biocompatible α-cyanacrylates, and the shell is manufactured of a biocompatible hydrophilic polymer, preferably of a copolymer of N-vinylpyrrolidon and/or derivatives of acrylic- and/or methacrylic acid. Biocompatible polymers of the core and shell can dissolve within human body, but their biodegradation resistance can be adjusted to exceed the functionality term of the therapeutic medicine, and furthermore, biodegradation rate of shell is lower than biodegradation rate of the transplant core. It is proved experimentally, that for instance a layer having a thickness of 1 mm comprising the copolymer of ethyl-α-cyanacrylate and ethoxyethyl-α-cyanacrylate (molar ratio=1:1) results in biodegradation corresponding to a proportion of 50% in 3-4 months. Under similar conditions, a copolymer of N-vinylpyrrolidon and butylacrylate leads to the same 50% biodegradation in 7-8 months. Taking furthermore into account that the average functionality term of the transplant is 1-3 months, bioavailability of insulin (its release from the transplant into the body tissues) will be primarily controlled by a uniform process of diffusion instead of biodegradation, the latter being difficult to regulate accurately. Furthermore, the programmed instability of the transplant core enables its gradual degradation and assimilation in form of non-toxic metabolites, thus eliminating the requirement according to the state of the art for subsequent surgical removal of the exhausted transplant.

EXAMPLE 1

A reaction mixture (50% of ethyl-α-cyanacrylate and 50% of ethoxyethyl-α-cyanacrylate, measured as weight-% (wt.-%)) was prepared, after which a calculated quantity of synthetic human insulin was added to the mixture at a temperature in the range of 0-4° C. while stirring the mixture. The resulting mixture was put over a polyethylene plate having a thickness in the range of 1-2 mm and subsequently left for 24 hours at a temperature of 20° C. The hardened mixture was crushed in a vibratory mill, after which a 50% (1:1) mixture of acetone and hexane was added, and the resulting substance was stored in a closed vessel for 3 hours while agitated until plastisol is formed. The plastisol was moulded into bars of 2.1-2.2 mm diameter under pressure, matured at room temperature, and then cut into pieces with a length in the range of 5-15 mm. Weight of the resulting bars was 30, 60, and 90 mg, with insulin contents of 50, 100 and 150 units (IU), correspondingly.

A 15% solution of the copolymer of N-vinylpyrrolidon and grade PPV butylmethacrylate in acetone was prepared and coated over the surface of insulin-containing rods as prepared above by dipping said rods into the polymer solution thrice and drying them for 1 hour between dippings. Thickness of the rods after the coating step increased to 2.6 mm. The rods were then sterilized by gas or radiation, using thereby the common standard techniques according to the state of the art.

Tests in vivo were performed on white rats with modeled alloxane diabetes corresponding to a glucose level of at least 350 mg-%. Concentration of glucose in blood plasma was determined by the common glucoseoxidase method. p The therapeutic rods with varying insulin content were implanted endermically into the nape of the neck of the rats.

Variations of glucose level in blood of the test rats were monitored for up to 40 days. During this term, 8, 10, and 12% of total insulin supply was released from the implanted rods. It is also remarkable to note, that in case of the 150 unit rods the glucose concentration in blood plasma was sustained at the level of 100-150 mg % for a significant time.

2. Second Aspect of the Present Invention

The second aspect of the present invention provides a means for treatment of diabetic patients, in order to provide a correction of the glucose concentration in their blood plasma, preferably a short term correction of the glucose concentration.

The second object of this invention is to provide especially a possibility for injectionless administration of insulin via the mucous membrane of the mouth cavity in order to correct the carbohydrate metabolism.

The aforementioned second object is achieved by adding low-molecular peptides promoting insulin transport through the mucous cell membranes to the diabetes treatment drugs containing insulin, preservatives, additives regulating insulin solubility and resistance to the enzymes of the mouth cavity, and a polymeric matrix in the film in order to provide adhesion to the mouth cavity surface. A good example for the low molecular peptides are cationic proteins extracted from *bovine thymus* during purification of chromatin-associated proteins soluble by acids. These cationic proteins can improve permeability of biological membranes, thereby serving as insulin transporters. The group of said cationic proteins comprises in particular cationic histones, currently produced as a well known prior art product for different requirements of pharmaceutical and cosmetic industries. Another type of said low-molecular, cationic proteins suitable for this invention are various cytomedins (usually designated in scientific literature as cytocines: in Russia manufactured for instance by Госу дарствeнньtū Меòико-Еuолозuнескuū Научно-Проusвоòсмвенньtū Комuлекс ЦИ ТОМЕД in cooperation with Завоò Меòчuнскuх Препаратое Санкт-Петербурзскozo Мясокомбuнамаuм Кuроsа), having preferably a molecular mass in the range of of 1,000-3,000 Dalton. Cytomedins are extracted from animal tissues (e.g., thymalin=extracted from thymus tissue, epitalamin=extracted from pineal gland tissue, renalin=extracted from kidney tissue, pancrealin=extracted from pancreas tissue, etc.).

The low-molecular peptides cause no chemical or conformational modifications of insulin molecules. Adding histones to the insulin-containing application films allows to achieve significant increase of biological availability of the drug with the following component proportions, indicated usually in weight-% (wt.-%), if not explicitly indicated differently:

| | |
|---|---|
| histone and/or cytomedin | 0.1-10.0 |
| insulin with conditional activity of 1 mg = 50 insulin units (IU) | 0.1-20.0 |
| preservatives | 0.1-15.0 |
| additives regulating insulin solubility | 0.01-5.0 |
| polymer matrix soluble by water | remainder |

The following preservatives preferably used can be comprised—alone or in a suitably selected combination—in the drug: phenol (0.1-1.0%); albumin (1-15%). The following additives regulating insulin solubility can preferably be used: hydrochloric or acetic acid (added until solution pH reaches a value in the range of about 2.0-4.0); glycine (1-10%); glucose (1-10%). The following polymeric matrices can preferably be used for the drug: copolymers of N-vinylpyrrolidone; acrylamide and/or ethylacrylate, the homopolymer of N-vinylpyrrolidon, polyether based on ethylene glycol and dibasic acids with a molecular mass in the range of 2,000-5,000 Dalton.

The above composition is applied as a dosed drug, preferably in the form of plates or films with a thickness in the range of 0.2-1 mm.

EXAMPLE 2

| Composition of the drug, mass % | |
|---|---|
| human insulin, genetically modified, activity of 1 mg = 50 insulin units (IU) | 0.5 |
| salazopyridazin | 0.02 |
| albumin | 1.0 |
| glycine | 1.0 |
| histone | 0.5 |
| phenol | 0.1 |
| HCl (0,1 n) | 0.01 |
| mixture containing a copolymer of N-vinylpyrrolidon, acrylamid and ethylacrylate (3:3:4) (80%), and homopolymer of N-vinylpyrrolidon (20%) | up to 100 |

An aqueous solution of the above composition with a concentration in the range of 15-20% and a pH-value of 4.0 is created by sequentially adding the components to the calculated quantity of water and agitating the mixture until the solution becomes homogenous. Then, a plate of inert material is covered by one or several layers of the solution and left to dry naturally at a temperature in the range of 18-40° C. until the residual humidity does not exceed 15%. The resulting film having a thickness of 1.5 mm is cut into oval-shaped plates (4.5 by 9 mm). Each plate weighs 60 mg and contains 12.5 insulin units (IU).

3. Third Aspect of the Present Invention

The third aspect of the present invention relates to the provision of special ways and means for diabetes treatment on the basis of a suitable combination comprising the above-discussed two aspects of the present invention.

The third object of the present invention is therefore the provision of a way and means of insulin deficiency correction in the diabetic mammal's organism or boundary forms of the broken tolerance of carbohydrates deprived of the above specified drawbacks. This object is achieved by the teaching in that the correction of the glucose concentration level in the diabetes mammal's organism is provided by the combined application of the means for maintenance of insulin concentration ensuring minimal constant therapeutic insulin level in the organism, preferably at least within 30 days, on the one hand, and the means for additional correction of insulin concentration relevant to physiological fluctuations of the glucose concentration in the blood plasma depending of food intake, physical and emotional stress, on the other hand. In said combination, first mentioned means is to be applied for long term correction preferably, and second mentioned means is to be applied for short term correction preferably. The combined use of two therapeutic means different by nature according to the third aspect of the present invention results in complete agreement with the features of natural, biochemical processes in the living organism connected with carbohydrate metabolism proceeding naturally on the basis on insulin participation.

In a healthy organism the glucose concentration ensuring the above specified processes lies within the certain borders (80-100 mg %). During the day, the glucose concentration can change from an average level depending on the release of carbohydrates into the organism, and/or in view of certain physical circumstances. These processes are usually regulated by adequately varying insulin amounts being released into the blood current.

A well known pathologic condition results in the disturbance of the level of the glucose concentration continiously present in the blood of a patient. The usual cyclic variation of this glucose concentration level during the period of one day is similarly affected as well. The means combination for the treatment of said pathologic condition in accordance with the present invention takes the above effects accurately into account. This means combination allows to correct said glucose concentration in the human plasma by means of influencing the insulin content. Actually, the continuous disturbance of the glucose concentration level can be overcome by applying the implantation means, whereas the disturbance of the usual cyclic variation of the glucose concentration level can be overcome simultaneously by means of periodically applying the application means. This results in the maintenance of the continuous glucose content level in blood, on the one hand, and also in the maintenance of the natural glucose concentration variation during the period of one day, on the other hand, whereby first mentioned means is to be applied for long-term correction preferably, and second mentioned means is to be applied for short-term correction preferably.

In comparison with the known methods for therapeutical treatment of diabetes mellitus according to the state of the art, the means combination as provided according to the teaching of the present invention has some advantages unexpectedly found, in particular the following ones:

1. The known means for treating diabetes according to the state of the art usually fix a certain, invariant level of the insulin concentration in blood, resulting in a corresponding, fixed level of scheduled glucose consumption in the body of the patient, whereas the means combination according to the present invention in contradiction to this disadvantage ensures the physiological character of the natural insulin concentration regulation, taking into due account the usual, natural variations in the biochemical processes due to the activities in living organisms.
2. The means combination according to the present invention is less complicated andmore reliable than the formerly used methods according to the state of the art (e.g., implantation of β-cells of a donor, implantation of mechanical devices, etc.). Implantation of β-cells of a donor requires a sophisticated process cascade, in order to prepare such an operation, in particular, the extraction of cells, the storage of said cells in a tissue deposition bank, the fulfillment of further, very strict requirements during the transportation of cells and a very special professional knowledge of the operating, surgical medicine. The said mechanical devices could be easily damaged, the costs are comparatively high, and the possible, dangerous side effects for the patient should never be underestimated. Furthermore, after the exhaustive of insulin supply, devices according to the state of the art require an additional, surgical operation, in order to remove them from the body of the patient, and/or to recharge them. The implication means for treatment of diabetes according to the present invention differs significantly from the devices according to the state of the art, because it is more resistant towards possible damages, it is easier to handle and additionally more reliable when applied. It is possible to introduce the means combination according to the present invention into the patient's body by means of a simple, undangerous ambulant method, requiring no further surgical operation for the subsequent removal from the body.

The means for the therapy of disturbances in the usual cyclic variation of glucose concentration provides additionally a simple possibility for the introduction of insulin into the organism of a mammal in need thereof without injection, in order to overcome the above-discussed disturbances. This procedure allows thereby an optimal adjustment of the administration of said means by the patient, taking into due account the individual health conditions and mental state of each single patient as well.

EXAMPLE 3

Artificial alloxane diabetes was caused in a white rat by means of an injection of a 5 wt.-% solution of alloxane, calculated on the base of 185 mg per kg body weight of the rat, into the nape of the neck of the rat, resulting in an initial glucose concentration of 620 mg % in the blood plasma.

The implication means according to the present invention in the form of a bar with a diameter of 2, 5 mm and a weight of 35 mg has been introduced under the skin of said animal by means of an injection needle with an inner diameter of 2, 6 mm. The means included 50 insulin units (IU). Three days after the injection, the glucose concentration in the plasma has been stabilized at a level in the range of 300 to 360 mg %.

In order to lower the glucose concentration, the means for the therapy of disturbances in the usual cyclic variation of glucose concentration has been introduced sublingually into the animal in form of a thin film (25 mg weight, content of 4 IU). The thin film was fixed on the mucous membrane by means of the surgical glue MK-7M in a manner being familiar for a skilled person. After 20 to 25 min., the glucose concentration was lowered to a value in the range of 135 to 140 mg %. Said level of the glucose concentration was invariant for one hour and then increased again up to the original level corresponding to a range of 320 to 350 mg % subsequently. A further application of the means for the therapy of disturbances in the usual cyclic variation of glucose concentration resulted in another, similar variation in the glucose concentration.

The invention claimed is:

1. A therapeutic preparation for maintaining a blood glucose concentration of a mammal in need thereof, the preparation comprising insulin and a polymeric matrix, characterized in that said polymeric matrix comprises a core comprising a biodegradable, hydrophobic polymer selected from the group consisting of $\alpha$-cyanacrylates, and an outer shell comprising a biodegradable, hydrophilic polymer selected from the group consisting of copolymers of N-vinylpyrrolidone and derivatives of acrylic- or methacrylic-acid, wherein said polymeric matrix results in biodegradation up to a proportion of not more than 50-wt. % during a period of one month.

2. The therapeutic preparation according to claim 1, characterized in that the insulin-containing core of the preparation has the form of a cylindrical rod or a sphere.

3. The therapeutic preparation according to claim 1, characterized in that the insulin-containing core comprises an insoluble polymer.

4. The therapeutic preparation according to claim 1, characterized in that the biodegradation rate of the shell is lower than the biodegradation rate of the core.

5. The therapeutic preparation according to claim 4, characterized in that the core comprises a copolymer of ethyl-$\alpha$-cyanacrylate, (molar ratio=1:1) resulting in biodegradation corresponding to a proportion of 50% in 3-4 months.

6. The therapeutic preparation of claim 4, characterized in that the shell comprises a copolymer of N-vinylpyrrolidone and butacrylate resulting in biodegradation corresponding to a proportion of 50% in 7-8 months.

7. The therapeutic preparation of claim 5, characterized in that the shell comprises a copolymer of N-vinylpyrrolidone and butacrylate resulting in biodegradation corresponding to a proportion of 50% in 7-8 months.

8. A therapeutic preparation for maintaining a blood glucose concentration of a mammal in need thereof, the preparation comprising insulin and a polymeric matrix, characterized in that said polymeric matrix comprises a core comprising a biodegradable, hydrophobic polymer of ethyl-$\alpha$-cyanacrylate and an outer shell comprising a biodegradable, hydrophilic polymer selected from the group consisting of copolymers of N-vinylpyrrolidone and derivatives of acrylic- or methacrylic-acid, wherein the biodegradation rate of the shell is lower than the biodegradation rate of the core, wherein the biodegradation rate of the core corresponds to a proportion of 50% in 3-4 months.

9. A therapeutic preparation for maintaining a blood glucose concentration of a mammal in need thereof, the preparation comprising insulin and a polymeric matrix, characterized in that said polymeric matrix comprises a core comprising a biodegradable, hydrophobic polymer selected from the group consisting of $\alpha$-cyanacrylates, and an outer shell comprising a biodegradable, hydrophilic polymer of N-vinylpyrrolidone and butacrylate, wherein the biodegradation rate of the shell is lower than the biodegradation rate of the core, wherein the biodegradation rate of the shell corresponds to a proportion of 50% in 7-8 months.

10. A therapeutic preparation for maintaining a blood glucose concentration of a mammal in need thereof, the preparation comprising insulin and a polymeric matrix, characterized in that said polymeric matrix comprises a core comprising a biodegradable, hydrophobic polymer of ethyl-$\alpha$-cyanacrylate, (molar ratio=1:1), and an outer shell comprising a biodegradable, hydrophilic polymer of N-vinylpyrrolidone and butacrylate, wherein the biodegradation rate of the shell is lower than the biodegradation rate of the core, wherein the biodegradation rate of the core corresponds to a proportion of 50% in 3-4 months and the biodegradation rate of the shell corresponds to a proportion of 50% in 7-8 months.

11. A therapeutic kit for diabetes treatment by insulin administration into a mammal resulting in a continuous optimization of the glucose level in blood, the kit comprising the following components:

1) a therapeutic preparation for maintenance of insulin concentration ensuring a minimal constant therapeutic insulin level in the organism, comprising insulin and a polymeric matrix, the matrix comprising a core comprising a biodegradable, hydrophobic polymer selected from the group consisting of α-cyanacrylates, and an outer shell comprising a biodegradable, hydrophilic polymer selected from the group consisting of copolymers of N-vinylpyrrolidone and derivatives of acrylic- or methacrylic acid, wherein said polymeric matrix results in biodegradation up to a proportion of not more than 50-wt. % during a period of one month; and 2) a therapeutic preparation for correction of insulin concentration adequate to physiological fluctuations of the glucose contents in blood plasma, said therapeutic preparation comprising insulin, a histone, and a polymeric matrix with a molecular mass in the range of 2,000-5,000 Daltons selected from the group consisting of copolymers of N-vinylpyrrolidone and acrylamide or ethylacrylate, homopolymers of N-vinylpyrrolidone, and polyethers based on ethylene glycol and dibasic acid.

12. The therapeutic kit according to claim 11, characterized in that the insulin-containing core of the therapeutic preparation of component 1) has the form of a cylindrical rod or sphere.

13. The therapeutic kit according to claim 11, characterized in that the insulin-containing core of the therapeutic preparation of component 1) comprises an insoluble polymer.

14. The therapeutic kit according to claim 11, characterized in that the biodegradation rate of the shell is lower than the biodegradation rate of the core for the therapeutic preparation of component 1).

15. The therapeutic kit according to claim 11, characterized in that said histone in the therapeutic preparation of component 2) has a molecular mass in the range of 1,000-3,000 Daltons.

16. The therapeutic kit according to claim 11, characterized in that the therapeutic preparation of component 2) the histone is present at a concentration in the range of 0.1-10.0 wt.-% based on the weight of the complete therapeutic preparation of component 1).

17. The therapeutic kit according to claim 11, characterized in that the therapeutic preparation of component 2) insulin with conditional activity of 1 mg=50 insulin unit (IU) is present at a concentration in the range of 0.1-20 wt.-% based on the weight of the complete therapeutic preparation of component 1).

18. The therapeutic kit according to claim 11, characterized in that the therapeutic preparation of component 2) is in the form of plates or films with a thickness of 0.2-1 mm.

* * * * *